(12) United States Patent
Groh et al.

(10) Patent No.: US 11,279,098 B2
(45) Date of Patent: Mar. 22, 2022

(54) METHOD FOR REDUCING THE MICROBIOLOGICAL LOADING OF CONTAINER PRODUCTS

(71) Applicant: KOCHER-PLASTIK MASCHINENBAU GMBH, Sulzbach-Laufen (DE)

(72) Inventors: Martin Groh, Gaildorf (DE); Christoph Bohn, Althuette (DE); Michael Spallek, Ingelheim (DE)

(73) Assignee: KOCHER-PLASTIK MASCHINENBAU GMBH, Sulzbach-Laufen (DE)

( * ) Notice: Subject to any disclaimer, the term of this patent is extended or adjusted under 35 U.S.C. 154(b) by 546 days.

(21) Appl. No.: 15/762,621

(22) PCT Filed: Sep. 8, 2016

(86) PCT No.: PCT/EP2016/001518
§ 371 (c)(1),
(2) Date: Mar. 23, 2018

(87) PCT Pub. No.: WO2017/054904
PCT Pub. Date: Apr. 6, 2017

(65) Prior Publication Data
US 2018/0297302 A1    Oct. 18, 2018

(30) Foreign Application Priority Data

Oct. 1, 2015   (DE) .................. 10 2015 012 939.2

(51) Int. Cl.
*B29C 71/04*    (2006.01)
*B29C 49/04*    (2006.01)
(Continued)

(52) U.S. Cl.
CPC ............... *B29C 71/04* (2013.01); *A61L 2/08* (2013.01); *A61L 2/14* (2013.01); *A61L 2/20* (2013.01);
(Continued)

(58) Field of Classification Search
CPC .......... A61L 2/08; A61L 2/14; A61L 2202/23; A61L 2/20; A61L 2202/023; B29C 71/04;
(Continued)

(56) References Cited

U.S. PATENT DOCUMENTS 3,897,889 A * 8/1975 Hindermann ....... B01F 13/1002
222/132
4,208,852 A * 6/1980 Pioch ....................... B29C 49/46
141/243
(Continued)

FOREIGN PATENT DOCUMENTS

DE       695 20 445     9/2001
DE       103 47 908     5/2005
(Continued)

OTHER PUBLICATIONS

Sculptify's Flex Flees Filament in Favour of Pellets https://3dprintingindustry.com/news/sculptifys-flex-flees-filament-favour-pellets-27618/ (Year: 2014).*
(Continued)

*Primary Examiner* — Thanh K Truong
*Assistant Examiner* — Scott A Howell
(74) *Attorney, Agent, or Firm* — Wenderoth, Lind & Ponack, L.L.P.

(57) ABSTRACT

A method reduces the microbiological loading of container products made at least partially of at least one plastic material. As part of a first production process, a plastic granulate (29) is fed to an extruder device (19), which melts the granulate (29). As part of a subsequent production
(Continued)

process, the melted granulate is forwarded onto a blow-molding, filling and sealing machine for obtaining the respective container product. At least in parts of the first production process, the plastic material undergoes at least one of the following treatment steps: high-energy radiation and/or plasma treatment and/or a gas having a sterilizing effect.

19 Claims, 2 Drawing Sheets

(51) Int. Cl.
    *B29C 49/46*     (2006.01)
    *B29C 49/00*     (2006.01)
    *A61L 2/08*     (2006.01)
    *A61L 2/14*     (2006.01)
    *A61L 2/20*     (2006.01)
    *B65B 55/02*     (2006.01)
    *B29K 101/12*     (2006.01)
    *B29L 31/00*     (2006.01)

(52) U.S. Cl.
    CPC .......... *B29C 49/0021* (2013.01); *B29C 49/04* (2013.01); *B29C 49/46* (2013.01); *B65B 55/02* (2013.01); *A61L 2202/23* (2013.01); *B29C 2049/4664* (2013.01); *B29K 2101/12* (2013.01); *B29L 2031/712* (2013.01)

(58) Field of Classification Search
    CPC ..... B29C 49/0021; B29C 49/04; B29C 49/46; B29C 2049/4664; B29C 49/002; B65B 55/02; B29L 2031/712; B29K 2101/12
    USPC .......................................................... 53/426
    See application file for complete search history.

(56) References Cited

U.S. PATENT DOCUMENTS

| | | | | |
|---|---|---|---|---|
| 4,759,887 A * | 7/1988 | Geissler | ................... | C01B 33/02 264/101 |
| 5,391,855 A * | 2/1995 | Tanisaki | ................... | B29C 59/14 156/345.48 |
| 5,703,009 A * | 12/1997 | Yvin | ................... | A01C 1/00 504/116.1 |
| 5,786,598 A * | 7/1998 | Clark | ................... | A23L 3/26 250/455.11 |
| 6,123,900 A * | 9/2000 | Vellutato | ................... | A61L 2/0011 250/455.11 |
| 6,145,276 A * | 11/2000 | Palm | ................... | B65B 55/04 422/24 |
| 6,814,559 B2 * | 11/2004 | Kossl | ................... | B29C 48/09 425/190 |
| 6,948,923 B2 * | 9/2005 | Lees | ................... | B29C 45/14336 425/112 |
| 7,682,696 B2 * | 3/2010 | Dean | ................... | A61L 2/28 428/412 |
| 7,744,365 B2 * | 6/2010 | Maddox | ................... | B29C 49/42 425/522 |
| 8,137,096 B2 * | 3/2012 | Hansen | ................... | B29C 49/70 425/537 |
| 10,441,689 B2 * | 10/2019 | Weisman | ................... | B29C 64/106 |
| 2004/0156879 A1 | 8/2004 | Muratoglu et al. | | |
| 2005/0241582 A1 * | 11/2005 | Dobbyn | ................... | C23C 4/134 118/723 E |
| 2007/0057411 A1 * | 3/2007 | Williams | ................... | B29B 13/00 264/483 |
| 2007/0212531 A1 * | 9/2007 | McIntyre | ................... | B29B 17/0042 428/297.4 |
| 2008/0258334 A1 * | 10/2008 | Hansen | ................... | B65B 3/022 264/209.1 |
| 2008/0283454 A1 * | 11/2008 | Muniak | ................... | B01J 49/75 210/86 |
| 2009/0214687 A1 * | 8/2009 | Eberlein | ................... | B29C 45/542 425/150 |
| 2010/0310701 A1 * | 12/2010 | Hansen | ................... | B29C 49/70 425/236 |
| 2011/0203579 A1 | 8/2011 | Quetel et al. | | |
| 2012/0245257 A1 * | 9/2012 | Fascio | ................... | B29B 9/12 524/35 |
| 2012/0294760 A1 * | 11/2012 | Humele | ................... | A61L 2/10 422/22 |
| 2013/0251927 A1 * | 9/2013 | Kouno | ................... | B29C 48/875 428/35.7 |
| 2014/0366485 A1 | 12/2014 | Chiang et al. | | |
| 2015/0239594 A1 * | 8/2015 | Batema | ................... | B65B 55/10 53/426 |
| 2016/0038655 A1 * | 2/2016 | Weisman | ................... | B29C 64/106 264/0.5 |
| 2018/0297302 A1 * | 10/2018 | Groh | ................... | B29C 49/0021 |

FOREIGN PATENT DOCUMENTS

| | | | | |
|---|---|---|---|---|
| DE | 10 2004 059 808 | | 6/2006 | |
| DE | 10 2005 013 701 | | 9/2006 | |
| DE | 10 2008 006 073 | | 7/2009 | |
| DE | 102008006073 | A1 * | 7/2009 | ............ B29C 49/70 |
| DE | 10 2008 032 635 | | 1/2010 | |
| DE | 10 2010 002 054 | | 8/2011 | |
| DE | 10 2011 008 132 | | 7/2012 | |

OTHER PUBLICATIONS https://www.ncbi.nlm.nih.gov/pmc/articles/PMC3416436/ (Year: 2012).*
https://www.cdc.gov/infectioncontrol/pdf/guidelines/disinfection-guidelines-H.pdf (Year: 2008).*
International Search Report (ISR) dated Nov. 18, 2016 in International (PCT) Application No. PCT/EP2016/001518.

* cited by examiner

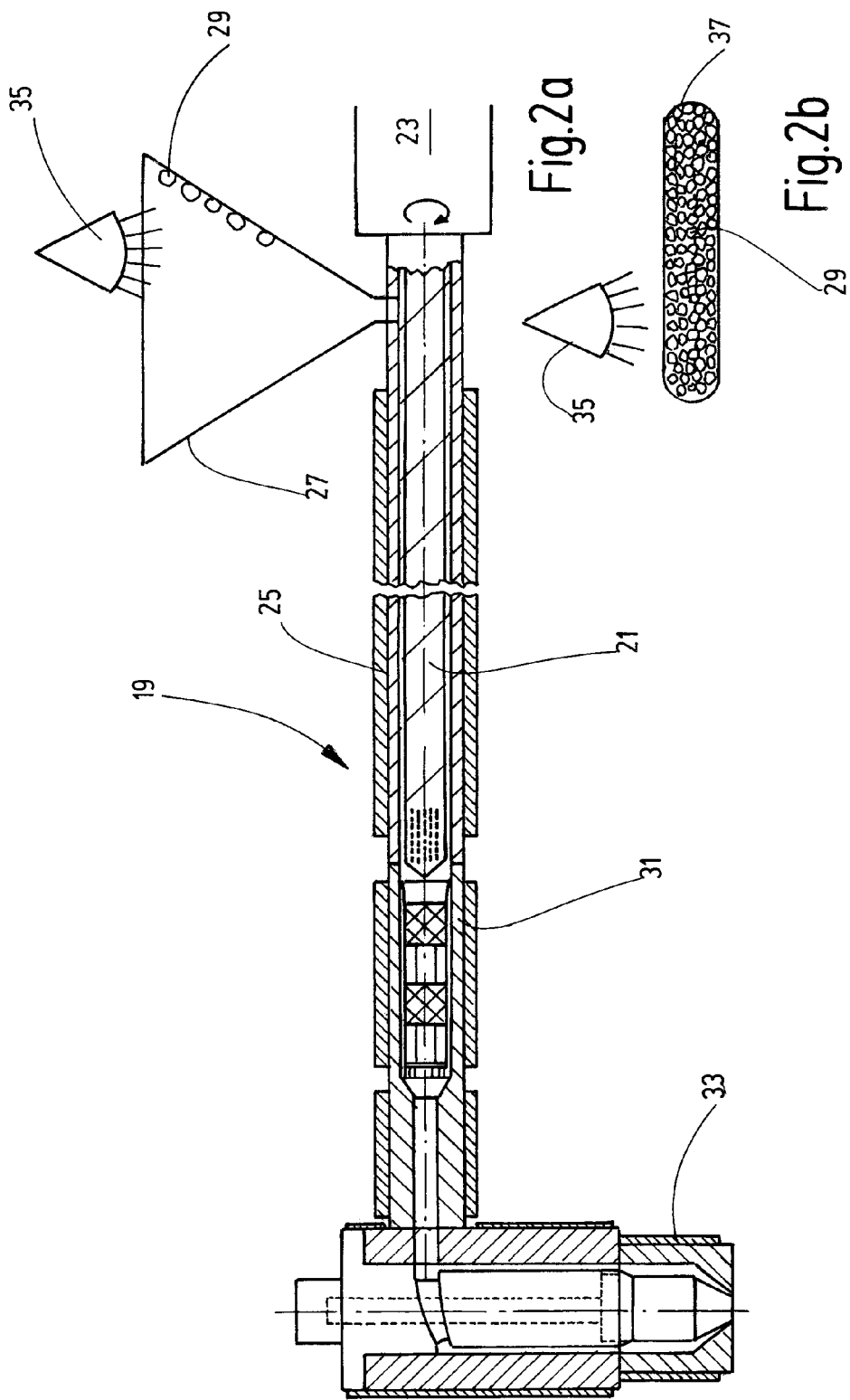

US 11,279,098 B2

METHOD FOR REDUCING THE MICROBIOLOGICAL LOADING OF CONTAINER PRODUCTS

FIELD OF THE INVENTION

The invention relates to a method for reducing the microbiological impact of container products, which are at least partially made from plastic material. As part of a first production chain, a plastic granulate is supplied to an extruder device, which melts the granulate. As part of an additional subsequent production chain, the granulate melt is transferred to a blow molding, filling and sealing production machine for forming the respective container product.

BACKGROUND OF THE INVENTION

When producing plastic containers, including ampule products for foods, cosmetics or for medicinal purposes, in particular ophthalmics, parenterals or for artificial feeding, the microbiological quality of the filling material is critically important. The specifications set out in the international pharmacopoeia must be satisfied. A decisive factor is firstly the sterility of the filling material before the filling, which can be achieved for example by sterile filtration. Another decisive factor is the sterility of the inner surfaces of the containers.

In this document, "microbiological contaminants" should be understood as a collective term to refer to bacteria, spores, yeasts, fungi, viruses and endotoxins, which were previously also referred to as pyrogens. The technical English term also used in this context is "bioburden".

The prior art has already provided suggestions for minimizing or largely preventing microbiological contaminants. For example, DE 10 2008 032 635 A1 describes a food and drinks industry method for the microbiologically optimized production of blow-molded plastic containers. This method involves the supply of a medium during the blowing operation for the plastic container to the inside of the corresponding premolding, which is for example in the form of air and at a temperature of between 80° C. and 140° C. This measure serves as a sterilization for the killing of germs. In order for this method to be effective, in view of the relatively low treatment temperatures, very long treatment times are required, certainly in the region of several hours, in order to ensure sustained killing of germs.

DE 10 2011 008 132 A1 describes a method for the production of blow-molded, at least partially sterile containers, in which method a premolding made of a thermoplastic material is initially heated and is then stretched by a stretching rod and has a pressurized fluid applied to it. A sterilizing agent is additionally supplied in the region of the premolding. The known method preferably uses as a sterilization agent vaporized hydrogen peroxide, which is mixed with hot air. The hydrogen peroxide concentration is approximately 15 to 35 percent by weight. The breakdown products of such chemical sterilization agents can contaminate the filling material and can have harmful toxicological consequences.

DE 695 20 445 T2 disclosed a method for the sterile packaging of a drink, in which method as part of the blow molding step for the container, the container is heated to a temperature sufficient to sterilize the inside of the container. Because a reliable sterilization requires temperatures significantly higher than 200° C. for a time period of several minutes, the choice of plastics for the container material for this known method is correspondingly limited. The polymers preferably used for the packaging of pharmaceuticals, such as polyethylene or polypropylene, cannot then be used at all due to their low working or melting temperatures.

DE 10 2008 006 073 A1 disclosed a blow molding, filling and sealing method (BFS method), which is particularly suitable for the production of filled containers for medicinal purposes. This method also includes ampules as container products for eye drops with filling volumes of, for example, 0.1 ml to 10 ml, as well as ampules for injection solutions in the range of typically 0.5 ml to 50 ml. Standard clock speeds for the production of such filled and sealed BFS containers are in the range of 10 to 18 seconds. In modern systems of the type disclosed in DE 10 2008 006 073 A1 however, the cycle time is only 2 to 4 seconds. Due to these low cycle times alone, the use of the above-mentioned known sterilization methods is ruled out, which methods then cannot be used for BFS methods because the container molding is immediately followed within a few seconds by the filling and a premolding or even an empty container is not available for a sterilization operation.

The microbiological status of containers produced according to the BFS method, was described in an article by Frank Leo et al. entitled "Evaluation of Blow-Fill-Seal Extrusion through Processing Polymer Contaminated with Bacterial Spores and Endotoxin", and published in the PDA-Journal of Pharmaceutical Science and Technology Vol. 58, No. 3, May-June 2004, pages 147 to 158 for the particular case of a BFS system of model 624 by the company Weiler Engineering with cycle speeds of 12 to 18 seconds (see page 148). Amongst other things, the specialist article discloses that reduction of spores occurs by two possible mechanisms, either thermal deactivation resulting from the long influence of heat during production (see page 153, bottom left) or as a result of the achieved homogeneous distribution (see page 153, $5^{th}$ paragraph) of the spores in the molten mass and an associated possible inactivation. In spite of this achieved homogeneous distribution, the authors report a germ count reduction in the region of only $10^2$ to $10^4$ colony-forming units per gram (cfu/g).

The results described above are, as the authors explicitly state, not transferable to other systems, in particular not to those BFS systems with significantly lower residence time at a raised temperature, for example, in the form of systems made by the company rommelag of model 460, which are the subject of the technical teaching according to DE 10 2008 006 073 A1. The clock speeds in that teaching, as stated above, are typically in the region of less than 5 seconds. In these systems, no cutting of the warm polymer tube occurs. The filling occurs by sterile filling tubes inside the intact plasticized polymer hose. The hose then in any case then constitutes a sterile barrier relative to the exterior space.

Unfortunately it is not, however, always possible to ensure that the polymer granulate used for the BFS process has a sufficiently minimal microbiological impact. It is then in practice possible, to some extent also as a result of incorrect transport, storage and handling of the plastic granulate, for microbiological contaminants, for example spores, to reach the granulate surface, which can lead to an undesirably high microbiological impact. The microbiological impact is not always adequately reduced by the previous BFS method according to the prior art.

SUMMARY OF THE INVENTION

Given this prior art, the problem addressed by the invention is to provide an improved method which, preferably as part of the BFS production process, can be integrated into same and which helps to significantly reduce the microbiological contaminants.

This problem is basically solved by a method where, at least in parts of the first production chain the respective plastic granulate used is subjected to at least one of the following treatment steps:
- a high-energy radiation and/or
- a plasma treatment and/or
- a gas having a sterilizing effect.

It is possible to achieve with each of these methods or treatment steps, with a relatively low technical expenditure, a significant reduction of microbiological contaminants within the plastic granulate, in particular on the surface thereof. There is no equivalent of this in the prior art.

In particular when the polymer granulate is treated with high-energy radiation, a reduction of microbiological contaminants on the granulate surface is obtained.

For the purpose of reducing microbiological contaminants, it is additionally possible to realize a plasma treatment, for example using a non-thermal, atmospheric plasma.

It is also possible to reduce the microbiological contaminants by chemical sterilization of the plastic granulate. This technique nevertheless in principle carries the risk of possible toxic residues in and on the produced container product including ampules.

The use of methods with high-energy radiation is advantageous in that the radiation of the polymers is not necessary. A conventionally occurring staining of polymers by high-energy radiation is not practically achievable, because on the one hand only low doses of radiation are required for the treatment of the granulate surface and on the other hand the immediately following thermal extrusion process as part of the blow molding, filling and sealing method leads to the "annealing" of active color centers. In a surprising manner it is then possible to also use such radiation methods on polymers that are in principle highly radiation-sensitive, such as polypropylene (PP) and on non-transparent or dyed polymers. It is then possible to dispense with the adaptation, which is complex in the radiating methods, of the radiation wave length to the respective container material.

It is also surprising for the average person skilled in the art of production of plastic container products that chain degradation reactions, which are in principle disadvantageous, are not observed in the radiation methods or in any case do not have a significant impact on the container quality.

Additional advantageous embodiments of the method according to the invention are disclosed hereinafter.

Other objects, advantages and salient features of the present invention will become apparent from the following detailed description, which, taken in conjunction with the drawings, discloses a preferred embodiment of the present invention.

BRIEF DESCRIPTION OF THE DRAWINGS

Referring to the drawings that form a part of this disclosure and that are schematic and not to scale:

FIG. 2a is a side view, depicted in a highly simplified manner and partially in section, of a conventional extruder device with an input-side filling funnel for plastic granulate and an output-side hose head, which discharges the melted plastic material at the input side on the top side of the BFS device according to FIG. 1; and FIG. 2b is a side view of a pouch-shaped package, depicted in a stylized manner, which is filled with plastic granulate for further processing with machine parts according to the depictions in FIGS. 1 and 2a and according to an exemplary embodiment of the invention.

DETAILED DESCRIPTION OF THE INVENTION

Figure 1:
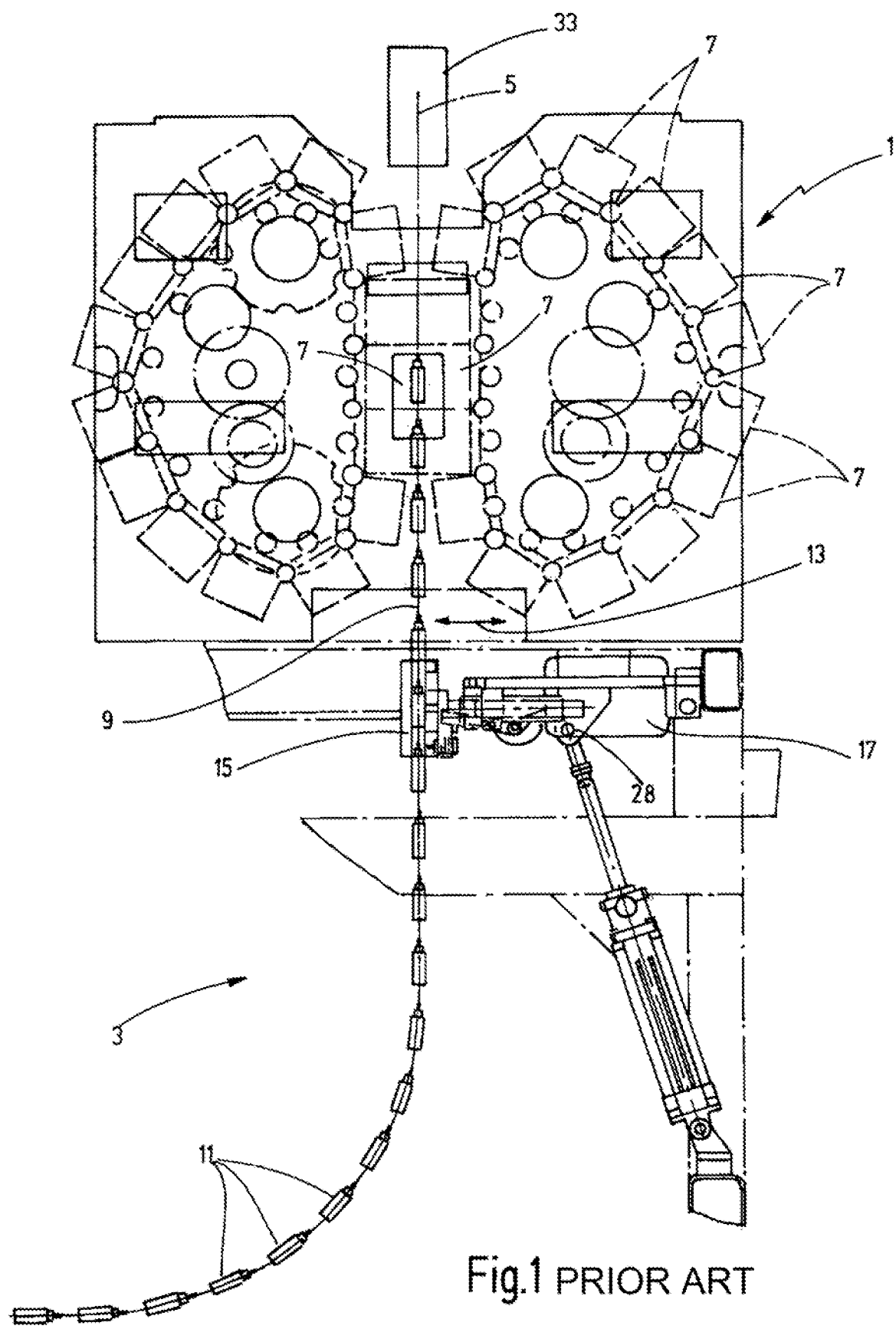
FIG. 1 is a side view, depicted in a highly simplified manner, of an exemplary embodiment of a blow molding, filling and sealing production machine according to DE 10 2008 006 073 A1 (production machines of model 460 from the company rommelag)

FIG. 1 depicts a production portion, lying at the top in the figure, and, connected thereto in the downwards direction, a demolding device 3. The production portion 1 is a machine device for carrying out a blow molding, filling and sealing method in accordance with the widely known Bottelpack® system. Specifically, in an embodiment in which various molding steps are carried out at various stations along a production line 5. In a type of carousel arrangement, individual molding parts 7, only a few of which are numbered in FIG. 1, are moved towards one another in pairs on a kind of virtual circular arc track in order to form a closed production mold, and are moved apart from one another again in order to open the mold. Because working machine devices that work in accordance with the Bottelpack® method are known per se, a more detailed explanation of the details of the production portion 1 of FIG. 1 is not necessary.

As can additionally be seen from FIG. 1, the container chain 9 formed by the individual molding parts 7 extends along the production line 5. At the bottom end of the production portion 1, the container chain 9 projects out of production portion 1 and arrives at the demolding device 3 at the input side. The container chain 9 can be a container chain track having a broad surface, in which a number of individual containers 11 of ampule-shaped form are arranged lying side by side next to each other as plastic container products in the container chain 9.

To assist with the detachment of the containers 11 from the walls of the individual molding parts 7 that move apart from one another at the output region, the demolding device 3 of the container chain 9 conveys a displacement movement, as is indicated in FIG. 1 with a double arrow 13. For this purpose, the demolding device 3 has a carrier arrangement 15 which, in geared connection with an electric drive motor 17, generates the displacement movement of the container chain 9 in order to reliably detach the containers 11 from the mold wall parts of the molding parts 7. Further details concerning the further construction of this production machine 1 together with the demolding device 3 can be obtained directly from document DE 10 2008 006 073 A1.

This blow molding, filling and sealing production machine 1 and demolding device 3 according to FIG. 1 forms, as part of the overall production method. An additional production chain 9 that connects to a first production chain, which, with its major components, is the subject of FIG. 2a. This first production chain comprises an extruder device 19 using a screw extruder. The screw conveyor 21 of the extruder can be driven by a drive 23. At the external circumference side, heating devices or heaters 25 are arranged on the rotatable screw conveyor 21 in order to plasticize or to melt the plastic granulate 29 supplied by a feeding hopper 27 or another filling device. While the feeding hopper 27 is located on the input side of the screw conveyor 21, a mixer device or mixer 31 is arranged on its output side 10. Mixer 13 transfers the plasticized or partially liquefied plastic material to a hose head 33, which is depicted in a simplified manner in FIG. 1 on the input side of the production portion 1. This hose head 33 conventionally has a discharge cross section in order to discharge the plastic as a curtain a plastic hose, closed at the casing side, to the production machine 1. For the sake of simpler depiction, the other production devices of the blow molding, filling and sealing production machine 1, for example, in the form of the filling pins for the introduction of the container material, are omitted, as were any blowing pins for producing the blowing mold and any vacuum devices present for improved contact of the plastic material on the mold inner wall of the individual molding parts 7. These production measures are known and will therefore not be addressed in further detail here.

The processing temperature of polyethylene as the plastic material used is 170° C. to 200° C. and is 190° C. to 200° C. in the case of polypropylene materials. The discharge pressure behind the extruder device 19 at the point of transition to the hose head 33 conventionally is approximately 200 bar to 400 bar.

As FIG. 2a additionally shows, a solution according to the invention involves plastic granulate or polymer granulate 29 being treated with high-energy radiation using a radiation source 35, which is symbolically included in the drawing. The radiation source 35 shall provide a high-energy radiation in order to achieve a reduction of microbiological contaminants of the kind described above to a large extent in the region of the granulate surface. This solution according to the invention is advantageously effective with little expenditure in that the plastic granulate or polymer granulate during the feeding to the extruder device 19 is dispersed or fanned out in a planar manner, for example, inside the feeding hopper 27 or as part of a granulate slide which is not depicted in detail but which is conventional. For this purpose a labyrinth guide (not depicted in detail) with obstacles may be helpful in order to then permit a preferably planar radiation source 35 to realize the radiation of the granulate 29 on at least one, and preferably several sides.

One possibility for the granulate treatment according to the invention by the radiation source 35 applies gamma rays, requiring a corresponding investment and safety costs. A safer option is the application of intensive ultra-short light flashes by xenon lamps with a high quantity of UV-C radiation, in particular in the wavelength range of 190 nm to 290 nm by the radiation source 35, which is essentially described in document U.S. Pat. No. 5,786,598 A.

The use of monochromatic UV light of 193, 222, 248, 282, 308 and 354 nm wavelength is also possible, as is essentially described in the US documents 2005/0173652 A1 and U.S. Pat. No. 8,125,333 B2 (B. Ressler et al). Another possibility is the application of X-rays via the radiation source 35 according to the essential specifications in the WO publication 2008/129397 A8.

It has proven to be particularly advantageous for the solution according to the invention to use electron beam sources, which are often also described as beta emitters. With relatively low electron beam energy, as it is sufficient to sterilize the granulate surface with only a low depth of penetration of a few micrometers into the actual plastic material, with the beta rays being applied once again via the radiation source 35.

The desired radiation dose—typically in the range from ca. 10 to 25 kGray—can be easily adjusted by appropriate dimensioning of the electron beam source 35 and of the residence times of the granulate 29 in the radiation zone. In the context of the method, which is also referred to in technical parlance as an E-beam method, compact electron beam lines with 80 kV to 300 kV acceleration voltage are preferably used, with which it is frequently possible to achieve a penetration depth up to about 300 µm in the polymer materials typically used in the BFS process. In the case of a 300 mm radiation length on a granulate slide (not depicted), 25 kGray was achieved at just 120 kV to 150 kV acceleration voltage. In a surprising manner, known, disadvantageous chain degradation reactions were not observed, even with polypropylene with the use of respective radiation via the radiation source 35, or did not in any case have a significant effect on the container quality of the individual containers 11 of the container chain 9.

Additionally or alternatively to the known radiation, a plasma treatment is also possible, with a non-thermal, atmospheric plasma preferably being used, as is described for example in the article by Tobias G. Klampfl et al. "Cold Atmospheric Air Plasma Sterilization against Spores and Other Microorganisms of Clinical Interest", published in the journal Applied and Environmental Microbiology, August 2012, Volume 78, No. 15 p. 5077-5082. In addition to the radiation source 35 or instead of same, an application device (not depicted in detail) is then employed for the atmospheric plasma to be created, which is to be introduced into or applied to the feeding hopper 27 or another feeding device for the extruder device 19. If only one plasma application process is to occur, the radiation source 35 can then be dispensed with in this respect.

It is furthermore possible to reduce the microbiological contaminants by chemical sterilization of the granulate. For this purpose, gases, such as ozone, hydrogen peroxide, ethylene oxide, nitrogen dioxide and other gases are used, as described for example in the CDC (Center Of Disease Control and Prevention) Guideline for Disinfection and Sterilization in Healthcase Facilities, 2008 by William A. Rutala et al. For the introduction of such gases, in the region of the feeding hopper 27 or another input device for the granulate 29 there is in turn provision of an input or application device (not depicted in detail) for this purpose.

As the depiction according to FIG. 2b shows, in principle the respective method according to the invention can also be used on a pouch-shaped package 37 with plastic granulate 29. The pouch-shaped package 37 also is able to remain closed in the context of the radiation method—in particular when gamma rays or X-rays are used, before the filling of the granulate 29 then occurs after radiation via the external radiation source 35 and opening of the package 37 by the filling device 27 into the extruder device 19.

In the context of a practical test of the solution according to the invention, for all of the exemplary embodiments materials, container sizes and machine settings were selected, which reflect the worst case concerning the mechanism of reduction of microbiological contaminants. As an example of microbiological contaminants, resistant spores of *Bacillus atrophaeus* and *Bacillus pumilus* were selected as test bacteria, as is standard in sterility testing. As container materials polymers, which have low BFS working temperatures, were additionally used in order to keep thermal effects on the artificially added spores low. In addition, process parameters were selected that have only minimal effects on the spores, but that result in container products having useable quality and standard output quantities. The throughput of polymer through the extruder 19 was then set at the upper limit in order to minimize the duration of the heat effect on the artificially added spores.

Furthermore, a BFS system of model 460 by the company rommelag, Waiblingen, Germany, was used with a cycle time for the container production of about 3.5 seconds. As plastic granulate 29 polymers were used, such as Purell LDPE of type 1840 H from the company LyondellBasell as well as Ineos LDPE of type Eltex MED PH 23H630, with working temperatures of the extruder 19 and of the hose head 33 in the range between 160° C. and 165° C. The thermoplastic polymer may be at least one of PE, HDPE, PP, PET, COC, COP, EVOH, PA or LDPE. The extruder may perform coextrusion forming a multi-layer wall of a filled and closed container product with an inner wall being a polymer.

In order to produce the contaminated granulate samples, endospores of the Bacillus atrophaeus ATTC 9372 with a D-value, $D_{160° C.}=0.285\pm0.08$ min were used. In a similar manner, spores of the reference germ for the radiation sterilization, Bacillus pumilus ATCC 27142, were used. The spores were evenly distributed on the granulate 29 and the spore quantity was verified in a laboratory. The concentration range was from $10^3$ to $10^6$ cfu per gram. 10 ml capacity containers 11 filled with 6 ml liquid CASO nutrient solution were produced.

For further clarification: CASO nutrient solution is a complex medium, to which is added, besides glucose, peptone proteolytically obtained from milk protein (casein peptone) and peptone proteolytically obtained from soy flour (soy flour peptone). The casein peptone is rich in free amino acids and the soy flour peptone is distinguished by a high carbohydrate and vitamin content. Such nutrient media are particularly well suited for the cultivation of fastidious microorganisms.

For each test batch, more than 12,000 container products were produced, with the analytical procedure otherwise corresponding to the contents of the above-mentioned article by Frank Leo et al "Evaluation of Blow-Fill-Seal-extrusion Through Processing Polymer Contaminated with Bacterial Spores and Endotoxin".

Firstly, three reference batches, i.e. without using the methods according to the invention, were produced for the purpose of germ reduction. For this purpose, a pin wrench distributer with holes, of the kind that is standard in extrusion technology, was used as a dynamic mixer device (as shown in the book by W. Michaeli), with no granulate treatment according to the invention taking place. This test resulted in a germ count reduction in particular due to thermal effects of on average $10^3$ cfu/gram.

In one of the tests, the polymer granulate 29 contaminated with Bacillus pumilus spores was then supplied via a vibrating slide, which is comparable to the feeding hopper 27, to the extruder device 19 and was radiated with an electron beam source 35 (e-beam) from the company Comet AG, Switzerland, in a contact-free manner, but only at a very small distance with different radiation doses of ca. 10, 15 or 25 or 30 kGray. At a 300 mm radiation length, 25 kGray with 140 kV acceleration voltage was achieved, the then-created ozone was extracted by suction. The contribution of the ozone to the germicidal action was not quantified, however it is generally not undesirable. If the ozone formation is undesirable for other reasons, this condition can be easily achieved in that air is replaced by an inert gas atmosphere formed of, for example, nitrogen, argon or carbon dioxide.

These tests showed that a rotating movement of the granules of the plastic granulate 29 and a flat fanning out of the granulate 29 is advantageous in order to prevent shadowing as much as possible, and then, to expose the entire surface of the granules to the high-energy radiation by the respective radiation source 35.

In addition, tests were realized using the electron beam source 35 described in detail above, in which tests spores of the Bacillus atrophaeus contaminated the polymer granulate 29.

The respective radiation method resulted in an improvement factor compared with the reference measurement described above of at least the factor 1000, i.e. 1000 times the quantity of biological contaminants were able to be destroyed.

All of the above-mentioned methods according to the invention for minimizing the microbiological impact have the advantage that it is not necessary to sterilize an empty plastic container or even an already filled container, but merely the still solid granulate before the melting.

When producing multi-layer containers according to the BFS method, as disclosed for example in document DE 103 47 908 A1, the use of the respective described reduction method according to the invention may suffice solely for the polymer granulate that forms the inner layer of the container 11.

A method for reducing the microbiological impact of plastic container products, produced according to the blow molding, filling and sealing method, in which, before discharge from the hose head 33, the plastic is subjected to a treatment step with gases having a sterilizing action, high-energy radiation and/or a plasma treatment, is not described in the prior art.

While one embodiment has been chosen to illustrate the invention, it will be understood by those skilled in the art that various changes and modifications can be made therein without departing from the scope of the invention as defined in the claims.

The invention claimed is:

1. A method for reducing microbiologicals in container products made at least partially of plastic material, the method comprising the following steps:
   supplying plastic granulate in pouch-shaped packages;
   treating the plastic granulate with radiation producing a sterilizing effect to reduce the microbiologicals in the plastic granulate when the plastic granulate is in the pouch-shaped packages;
   opening the pouch-shaped packages after the treating;
   after opening the pouch-shaped packages, emptying the plastic granulate from the pouch-shaped packages into a screw conveyer of an extruder and then melting the plastic granulate in the extruder into melted plastic; and
   after the melting of the plastic granulate in the extruder, transferring the melted plastic from the extruder to a blow molding, filling and sealing production machine forming filled container products.

2. A method according to claim 1 wherein
   the plastic granulate in the pouch-shaped packages is supplied to a planar conveyor or a hopper of the extruder.

3. A method according to claim 1 wherein
   the treating is with the radiation, the radiation being applied as at least one of gamma radiation, UV radiation, monochromatic UV radiation, X-rays, or a sequence of rapid light flashes.

4. A method according to claim 1 wherein
   the treating takes place while the plastic granulate is separated by movement, with the treating being along parts of surfaces of the plastic granulate with an infiltration depth.

5. A method according to claim 1 wherein
   the plastic granulate is a thermoplastic polymer.

6. A method according to claim 5 wherein the thermoplastic polymer is at least one of PE, HDPE, PP, PET, COC, COP, EVOH, PA or LDPE.

7. A method according to claim 1 wherein the method is conducted in a sterile manner with production cycle times for a, filled and closed container product of 2 to 4 seconds.

8. A method according to claim 1 wherein the extruder performs coextrusion forming a multi-layer wall of a filled and closed container product with an inner wall being a polymer.

9. A method for reducing microbiologicals in container products made at least partially of plastic material, the method comprising the following steps:

supplying pellets of plastic granulate onto a planar inclined feeding wall of a hopper or slide with the pellets of the plastic granulate being dispersed from one another in a planar manner on the inclined feeding wall;

treating the pellets of the plastic granulate with a least one of a radiation, a plasma treatment, or a gas having a sterilizing effect to reduce the microbiologicals in the plastic granulate, the treating taking place when the pellets of the plastic granulate are disposed from one another on the inclined feeding wall;

transferring the pellets of the plastic granulate from the inclined feeding wall, after the treating of the pellets of the plastic granulate, to an extruder and then melting the pellets of the plastic granulate in the extruder into melted plastic; and transferring the melted plastic from the extruder after the melting of the pellets to a blow molding, filling and sealing production machine forming filled container products.

10. A method according to claim 9 wherein the treating is with the radiation, the radiation being applied as at least one of gamma radiation, UV radiation, monochromatic UV radiation, X-rays, or a sequence of rapid light flashes.

11. A method according to claim 9 wherein the treating is by the plasma treatment, the plasma treatment being an atmospheric plasma.

12. A method according to claim 9 wherein the treating is by the gas having the sterilizing effect, the gas having the sterilizing effect being at least one of ozone, hydrogen peroxide, ethylene oxide or nitrogen dioxide.

13. A method according to claim 9 wherein the treating takes place while the plastic granulate is separated by movement, with the treating being along parts of surfaces of the plastic granulate with an infiltration depth.

14. A method according to claim 9 wherein the plastic granulate is a thermoplastic polymer.

15. A method according to claim 13 wherein the thermoplastic polymer is at least one of PE, HDPE, PP, PET, COC, COP, EVOH, PA or LDPE.

16. A method according to claim 9 wherein the method is conducted in a sterile manner with production cycle times for a, filled and closed container product of 2 to 4 seconds.

17. A method according to claim 9 wherein the extruder performs coextrusion forming a multi-layer wall of a filled and closed container product with an inner wall being a polymer.

18. A method according to claim 9 wherein the pellets are treated with radiation at a dose of at least 10 to 25 kGray.

19. A method according to claim 9 wherein the plastic granulate are treated with radiation at a dose of at least 10 to 25 kGray.

* * * * *